US009563979B2

(12) United States Patent
Davey

(10) Patent No.: US 9,563,979 B2
(45) Date of Patent: Feb. 7, 2017

(54) APPARATUS AND METHOD FOR REGISTERING VIRTUAL ANATOMY DATA

(71) Applicant: Toshiba Medical Systems Corporation, Otawara-shi (JP)

(72) Inventor: Robert Davey, Edinburgh (GB)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/555,872

(22) Filed: Nov. 28, 2014

(65) Prior Publication Data

US 2016/0155236 A1    Jun. 2, 2016

(51) Int. Cl.
| | |
|---|---|
| G06K 9/00 | (2006.01) |
| G06T 15/08 | (2011.01) |
| G06T 17/20 | (2006.01) |
| G06T 7/00 | (2006.01) |
| A61B 5/055 | (2006.01) |
| A61B 8/00 | (2006.01) |
| A61B 5/00 | (2006.01) |
| A61B 6/03 | (2006.01) |

(52) U.S. Cl.
CPC .............. *G06T 15/08* (2013.01); *G06T 7/0028* (2013.01); *G06T 17/20* (2013.01); *A61B 5/055* (2013.01); *A61B 5/743* (2013.01); *A61B 5/744* (2013.01); *A61B 6/032* (2013.01); *A61B 8/00* (2013.01); *G06T 2207/10072* (2013.01); *G06T 2207/10081* (2013.01); *G06T 2207/30004* (2013.01); *G06T 2215/16* (2013.01)

(58) Field of Classification Search
None
See application file for complete search history.

(56) References Cited

U.S. PATENT DOCUMENTS

| | | | | |
|---|---|---|---|---|
| 6,522,780 | B1* | 2/2003 | Pass .................. | G06F 17/30256 382/170 |
| 7,158,692 | B2* | 1/2007 | Chalana .................. | G06K 9/00 382/128 |
| 7,523,505 | B2* | 4/2009 | Menschik ............. | G06F 19/322 705/3 |
| 8,698,795 | B2* | 4/2014 | Grewer ................. | G06T 7/0081 345/419 |
| 2004/0109594 | A1* | 6/2004 | Luo ....................... | G06T 7/0081 382/132 |

(Continued)

OTHER PUBLICATIONS

Dr. Robi Kelc, "Zygote Body: A New Interactive 3-Dimensional Didactical Tool for Teaching Anatomy" WebmedCentral Anatomy, 2012, 3(1) WMC002903, pp. 1-10.

(Continued)

*Primary Examiner* — Nancy Bitar
(74) *Attorney, Agent, or Firm* — Oblon, McClelland, Maier & Neustadt, L.L.P.

(57) ABSTRACT

An image processing apparatus comprises a data receiving unit configured to receive medical imaging data and a registration unit configured to obtain a registration of the medical imaging data with model-based virtual anatomy data by determining a transformation between a coordinate space of the medical imaging data and a coordinate space of the virtual anatomy data based on the locations of anatomical landmarks in the medical imaging data and the locations of corresponding anatomical landmarks in the virtual anatomy data.

25 Claims, 6 Drawing Sheets

(56) References Cited

U.S. PATENT DOCUMENTS

| | | | |
|---|---|---|---|
| 2005/0027492 A1* | 2/2005 | Taylor | G06K 9/48 703/2 |
| 2005/0207658 A1* | 9/2005 | Schofield | G06F 19/321 382/232 |
| 2006/0229911 A1* | 10/2006 | Gropper | G06F 19/321 705/2 |
| 2007/0064987 A1* | 3/2007 | Esham | A61B 6/481 382/128 |
| 2007/0086678 A1* | 4/2007 | Chefd'hotel | G06K 9/6289 382/294 |
| 2008/0052112 A1* | 2/2008 | Zahlmann | G06F 19/321 705/2 |
| 2008/0089566 A1* | 4/2008 | Node-Langlois | G06T 7/0024 382/128 |
| 2008/0119712 A1* | 5/2008 | Lloyd | A61B 19/52 600/407 |
| 2009/0149977 A1* | 6/2009 | Schendel | G06F 19/3437 700/98 |
| 2010/0295848 A1* | 11/2010 | Grewer | G06T 7/0081 345/419 |
| 2011/0110572 A1* | 5/2011 | Guehring | A61B 6/5258 382/131 |
| 2011/0188715 A1* | 8/2011 | Shotton | G06K 9/00 382/128 |
| 2012/0014559 A1* | 1/2012 | Suehling | G06K 9/6207 382/103 |
| 2012/0197619 A1* | 8/2012 | Namer Yelin | G06F 19/3437 703/11 |
| 2013/0211792 A1* | 8/2013 | Kang | G06F 19/3437 703/1 |
| 2014/0043329 A1* | 2/2014 | Wang | G06T 17/20 345/420 |
| 2014/0314290 A1 | 10/2014 | Dabbah et al. | |
| 2015/0043772 A1 | 2/2015 | Poole et al. | |
| 2015/0185846 A1* | 7/2015 | Otto | G06F 3/016 345/156 |
| 2016/0000515 A1* | 1/2016 | Sela | G06T 7/0028 600/424 |

OTHER PUBLICATIONS

Victor Spitzer, et al., "The Visible Human Male: A Technical Report" Journal of the American Medical Informatics Association, vol. 3, No. 2, Mar./Apr. 1996, pp. 118-130.

Aviv Hurvitz, "Registration of a CT-like atlas to fluoroscopic X-ray images using intensity correspondences" The Hebrew University of Jerusalem, Aug. 2008, pp. 1-80 with Cover Pages.

K. Subburaj, et al., "Automated identification of anatomical landmarks on 3D bones models reconstructed from CT scan images" Computerized Medical Imaging and Graphics, vol. 33, Jul. 2009, pp. 359-368.

"Vining aims to change radiology's perspective with ViSion" Aunt Minnie Website, Feb. 2012, 5 Pages.

Jonathan C. Silverstein, et al. "Enhancing Radiological Volumes with Symbolic Anatomy Using Image Fusion and Collaborative Virtual Reality" Medicine Meets Virtual Reality 12, 2004, pp. 347-352.

Mohammad A. Dabbah, et al., "Detection and location of 127 anatomical landmarks in diverse CT datasets" Medical Imaging 2014: Image Processing, vol. 9034, Mar. 21, 2014, pp. 903415-1-903415-11.

Antonio Criminisi, et al., "Regression Forests for Efficient Anatomy Detection and Localization in CT Studies" Medical Computer Vision, Recognition Techniques and Applications in Medical Imaging, 2011, pp. 106-117.

René Donner, et al., "Global localization of 3D anatomical structures by pre-filtered Hough Forests and discrete optimization" Medical Image Analysis, vol. 17, No. 8, 2013, pp. 1304-1314.

David Liu, et al., "Anatomical Landmark Detection Using Nearest Neighbor Matching and Submodular Optimization" Medical Image Computing and Computer-assisted Intervention, vol. 7512, 2012, pp. 393-401.

W. Paul Segars, et al., "MCAT to XCAT: The Evolution of 4-D Computerized Phantoms for Imaging Research" Proceeding of the IEEE, vol. 97, No. 12, Dec. 2009, pp. 1954-1968.

"Air Data Fusion package" Automated Image Registration, Retrieved Jun. 16, 2015, 2 Pages.

* cited by examiner

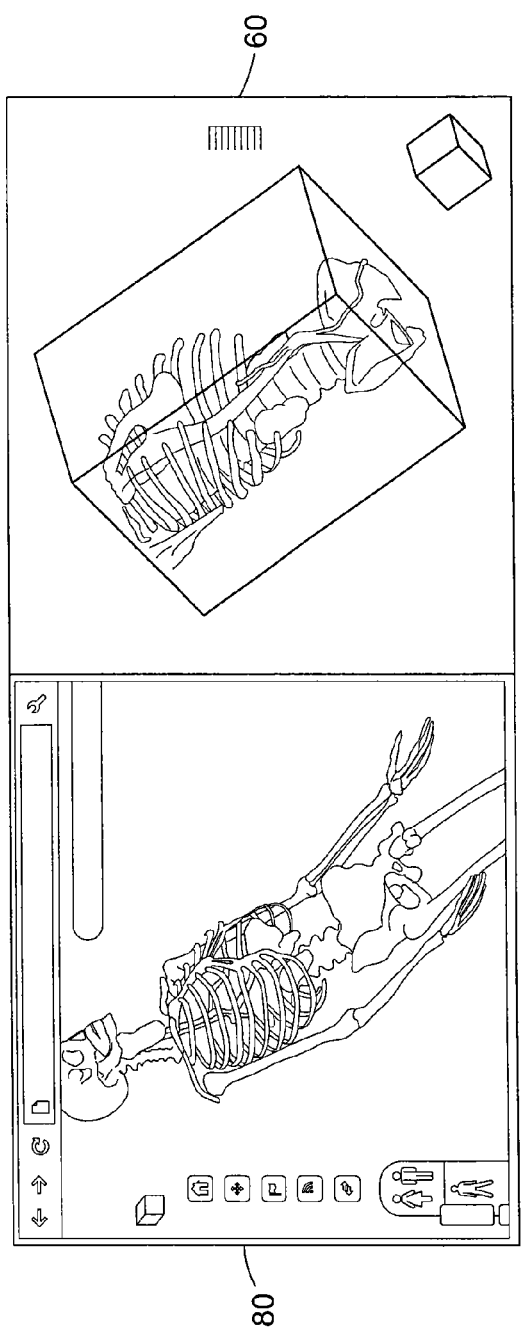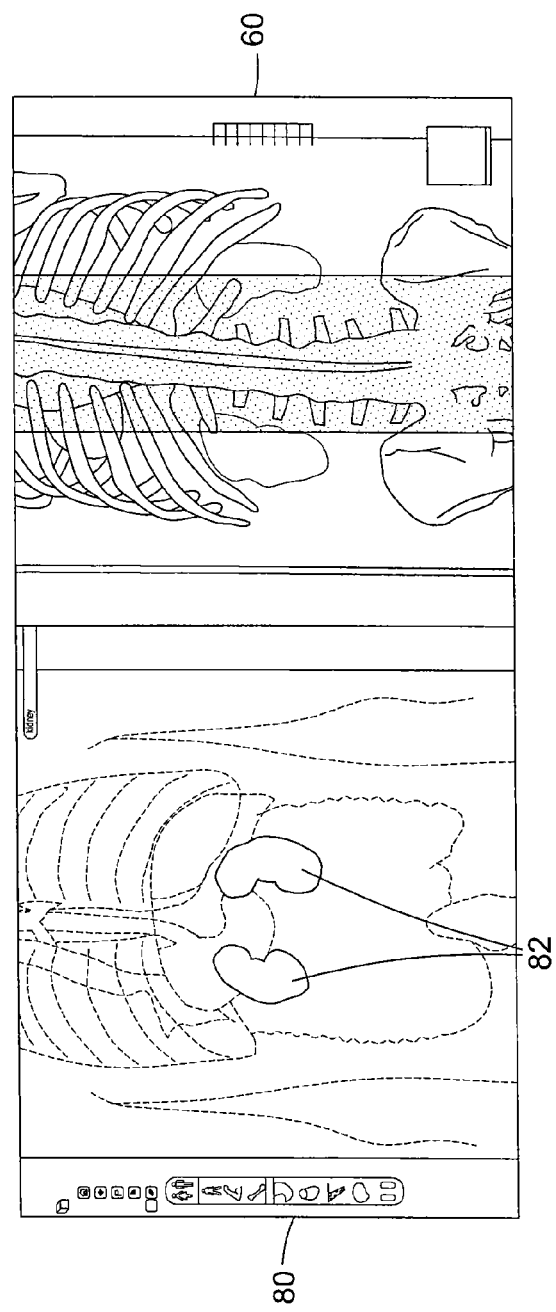

APPARATUS AND METHOD FOR REGISTERING VIRTUAL ANATOMY DATA

FIELD

Embodiments described herein relate generally to a method of, and apparatus for, registering medical imaging data with virtual anatomy data.

BACKGROUND

It is well known to use medical imaging techniques to obtain imaging data that is representative of anatomical structures within the body of a patient or other subject. Volumetric imaging data may, for example, be obtained by the acquisition of a series of two-dimensional slices (usually axial), which may be combined to form a three-dimensional array of voxels.

Volumetric imaging modalities may comprise, for example, computed tomography (CT), cone-beam computed tomography (CB-CT), magnetic resonance (MR) or ultrasound. In a CT data set, for example, each voxel usually has an associated intensity, measured in Hounsfield Units, which represents the attenuation of X-ray radiation by the respective, corresponding measurement volume.

Medical imaging data may be specific to a particular patient, and to a particular scan of that patient.

Medical imaging data can be in a variety of forms and can include any suitable data obtained from measurements by a medical imaging modality. Medical imaging data may be data that can be rendered, or otherwise processed, to obtain an image of at least part of a subject.

A virtual anatomy provides a representation of the location of anatomical features and may, for example, comprise a synthetic, non-patient-specific representation of generic human anatomy in three dimensions. A virtual anatomy may provide features such as the identification of organs and other anatomical structures. Anatomical structures (for example, the liver or other organs) may be named in the virtual anatomy. Anatomical structures may be given a shape and a position within the body.

Volumetric virtual anatomy data may comprise a set of voxels, for example a three-dimensional array of voxels, that may be similar to the three-dimensional array of voxels obtained through a medical imaging scan. For example, each voxel in the volumetric virtual anatomy data may have an associated intensity value. In volumetric virtual anatomy data, voxels may be assigned to anatomical structures within the human body, for example to provide a generic representation of the human body in which anatomical structures are segmented.

It is known to map volumetric patient data comprising an array of voxels to volumetric virtual anatomy data comprising an array of voxels, for example using similar registration techniques to those that may be used to register one set of volumetric patient data to another set of volumetric patient data. One approach to mapping volumetric patient data to volumetric virtual anatomy data is to use image similarity-based registration techniques, for example optimization based on mutual information. Image-based registration techniques may be computationally intensive, and therefore may be slow.

Other types of virtual anatomy data are known, in addition to volumetric virtual anatomy data comprising an array of voxels. For example, model-based virtual anatomy data is known in which anatomical structures are represented by models, for example surfaces or regions in three-dimensional space, rather than by labeled arrays of voxels.

BRIEF DESCRIPTION OF THE DRAWINGS

Embodiments are now described, by way of non-limiting example, and are illustrated in the following figures, in which:

FIG. 5 is an illustration of a side-by-side display of virtual anatomy data and medical imaging data;

FIG. 6 is an illustration of a further side-by-side display of virtual anatomy data and medical imaging data;

DETAILED DESCRIPTION

Certain embodiments provide an image processing apparatus, comprising a data receiving unit configured to receive medical imaging data and a registration unit configured to obtain a registration of the medical imaging data with model-based virtual anatomy data, wherein obtaining a registration of the medical imaging data and the virtual anatomy data comprises determining a transformation between a coordinate space of the medical imaging data and a coordinate space of the virtual anatomy data based on the locations of anatomical landmarks in the medical imaging data and the locations of corresponding anatomical landmarks in the virtual anatomy data.

Certain embodiments provide an image processing method, comprising receiving medical imaging data and obtaining a registration of the medical imaging data with model-based virtual anatomy data, wherein obtaining a registration of the medical imaging data and the virtual anatomy data comprises determining a transformation between a coordinate space of the medical imaging data and a coordinate space of the virtual anatomy data based on the locations of anatomical landmarks in the medical imaging data and the locations of corresponding anatomical landmarks in the virtual anatomy data.

Figure 1:
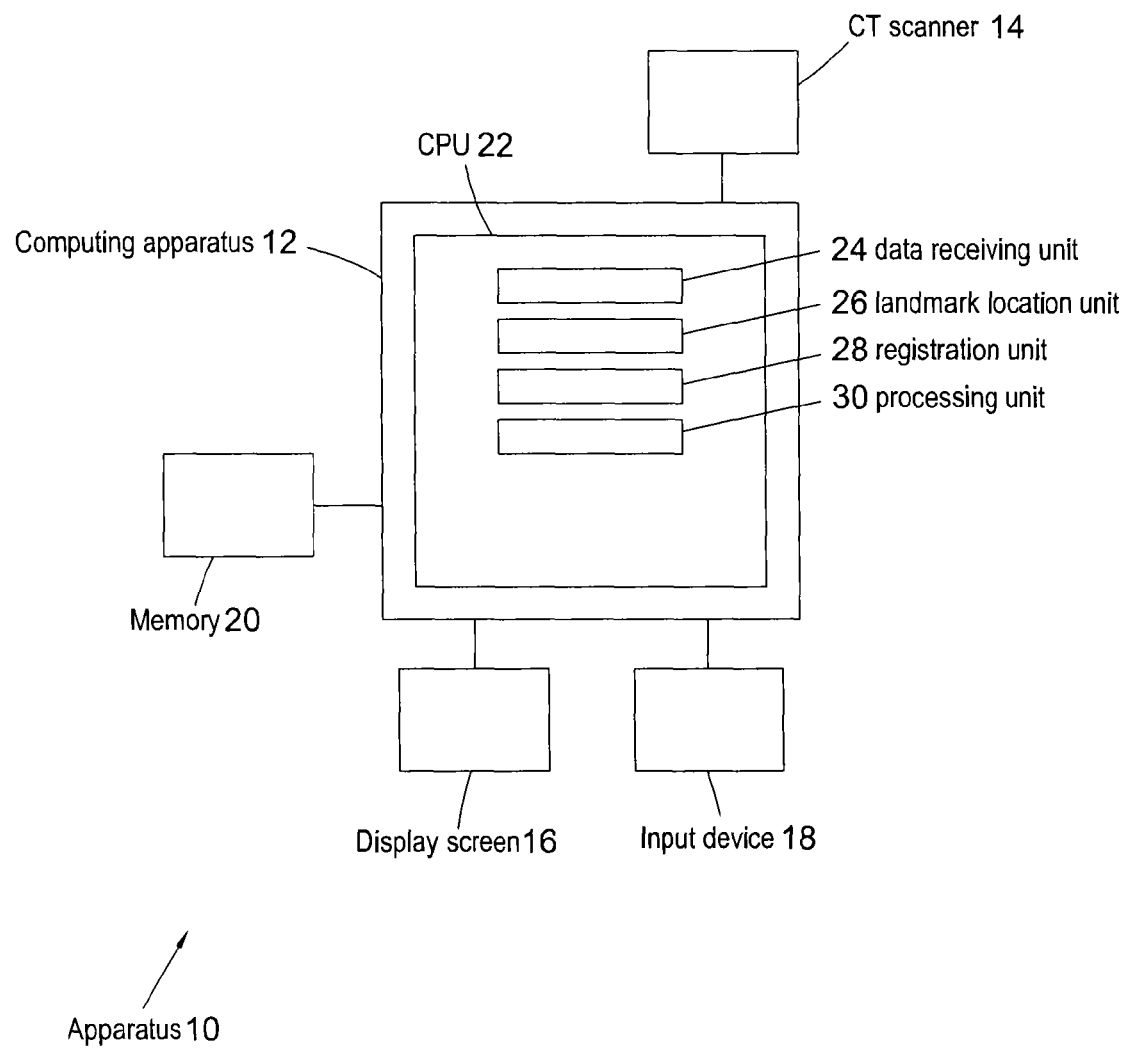
FIG. 1 is a schematic diagram of an imaging data processing system according to an embodiment.

An imaging data processing apparatus 10 according to an embodiment is illustrated schematically in FIG. 1. The image processing apparatus 10 comprises a computing apparatus 12, in this case a personal computer (PC) or workstation, that is connected to a CT scanner 14, a display screen 16 and an input device or devices 18, such as a computer keyboard and mouse. In the present embodiment, sets of imaging data are obtained by the CT scanner 14 and stored in memory store 20. In other embodiments, sets of imaging data may be loaded from a remote memory store.

Computing apparatus 12 provides a processing resource for receiving, registering and displaying medical imaging data and virtual anatomy data. Computing apparatus 12 comprises a central processing unit (CPU) 22 that is operable to load and execute a variety of software modules or other software components that are configured to perform the method that is described below with reference to FIG. 2.

The computing apparatus 12 includes a data receiving unit 24 for receiving medical imaging data, a landmark location unit 26 for locating landmarks within the medical imaging data, a registration unit 28 for registering the medical imaging data to a virtual anatomy, and a processing unit 30 for rendering and displaying images from the medical imaging data and/or virtual anatomy data.

In the present embodiment, the data receiving unit 24, landmark location unit 26, registration unit 28 and processing unit 30 are each implemented in computing apparatus 12 by at least one computer program having computer-readable instructions that are executable by the CPU 22. However, in other embodiments, the various units may be implemented as one or more ASICs (application specific integrated circuits) or FPGAs (field programmable gate arrays), or as any other suitable combination of software and hardware.

The computing apparatus 12 also includes a hard drive and other components of a PC including RAM, ROM, a data bus, an operating system including various device drivers, and hardware devices including a graphics card. Such components are not shown in FIG. 1 for clarity.

Figure 2:
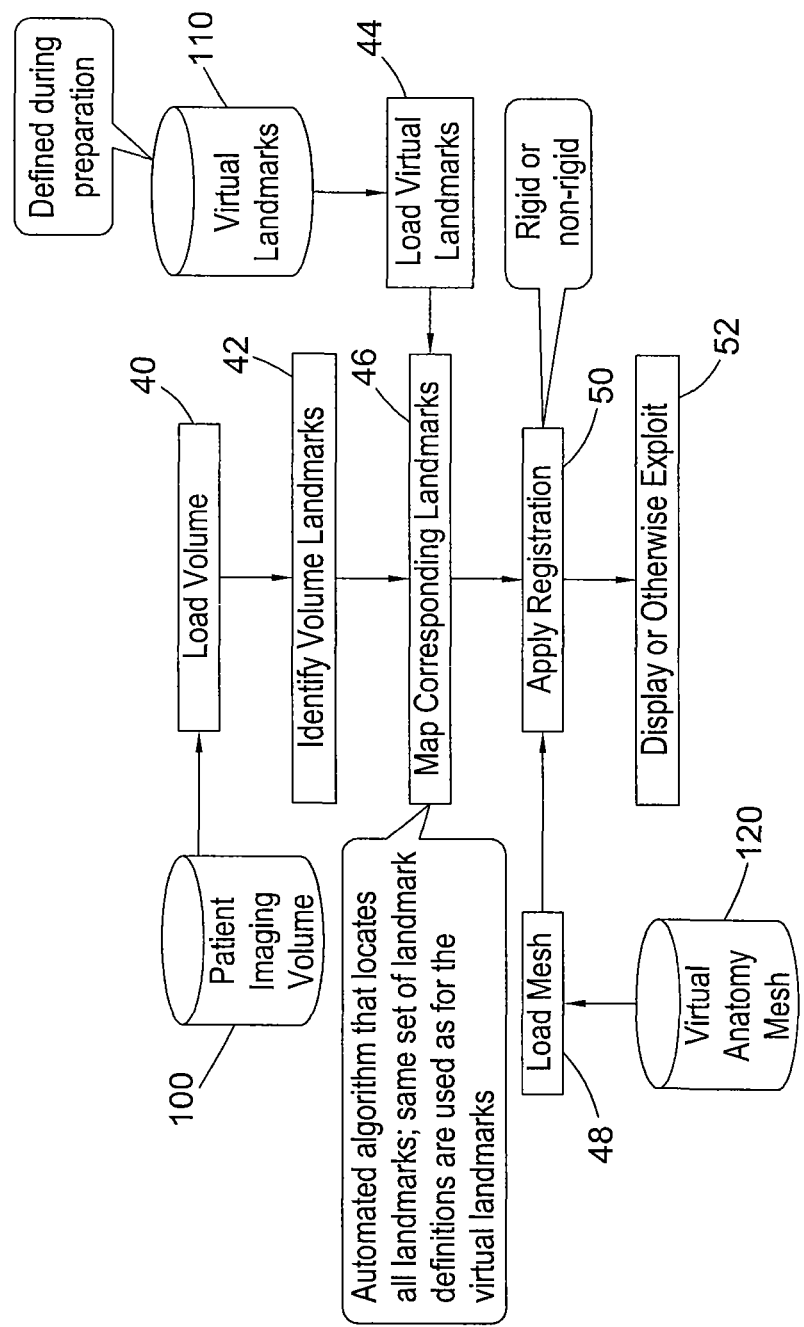
FIG. 2 is a flowchart illustrating in overview a mode of operation of an embodiment.

The system of FIG. 1 is configured to perform a series of stages as illustrated in overview in the flow chart of FIG. 2.

At stage 40 of FIG. 2, the data receiving unit 24 receives from memory store 20 a volumetric medical imaging data set 100 (indicated in FIG. 2 as patient imaging volume 100) obtained from a CT scan of a patient. The imaging data set 100 may comprise a series of DICOM (Digital Imaging and Communications in Medicine) files. In other embodiments, the data receiving unit 24 receives the imaging data set 100 from a remote data store, for example from a server which may form part of a Picture Archiving and Communication System (PACS). In further embodiments, the data receiving unit 24 receives the imaging data set 100 directly from the scanner 14.

In the present embodiment, the imaging data set 100 was obtained from a CT scan taken using CT scanner 14, which is connected to image processing apparatus 10. In alternative embodiments, the CT scan is taken using any CT scanner. In other embodiments, the imaging data set 100 comprises data obtained from any radiological scanner that produces volumetric radiological data in any modality, for example CT, MRI, ultrasound, PET or SPECT.

At stage 42, the landmark identification unit 26 uses a landmark location algorithm to automatically identify known anatomical landmarks in the imaging data set 100 and to determine the location of each anatomical landmark in the coordinate system of the imaging data set 100.

An anatomical landmark is usually a well-defined point in an anatomy (in the present embodiment, the human anatomy). Anatomical landmarks may be defined anatomically, in relation to anatomical structure such as bones, vessels or organs. Examples of anatomical landmarks include the center of the right eye and the apex of the right lung. The anatomical definition of a landmark may be used to locate that landmark in many different medical imaging data sets, or in virtual anatomies. For example, if the center of the right eye is determined as an anatomical landmark, the landmark at the center of the right eye may be located in any medical imaging data set or virtual anatomy in which the center of the right eye is present, by any manual or automatic method that can locate that point in the anatomy.

An anatomical landmark may be located in a data set and assigned a set of coordinates in the coordinate frame of that data set. The location of the anatomical landmark may be regarded as a point in coordinate space. It may be expected that the coordinate values for the anatomical landmark in one data set will differ from the coordinate values for the anatomical landmark in a different data set. For example, the coordinates of the anatomical landmark may differ due to differences in patient anatomy or patient positioning. In some embodiments, although a landmark may comprise coordinate data representing a location in a coordinate space of a volumetric data set comprising a set of voxels or other imaging data, the landmark may not itself include any of those voxels or imaging data.

The anatomical definition of each anatomical landmark may be pre-determined by clinical experts, and each landmark has a clear identity. Different anatomical landmarks, and different numbers of anatomical landmarks, may be determined for different applications. Each anatomical landmark may be defined anatomically on a generic human body.

The present embodiment uses a set of 127 known anatomical landmarks (anatomical landmarks for which anatomical definitions have been pre-determined). In other embodiments, a different set of anatomical landmarks may be used, which may comprise different landmarks (for example, the center of the right eye may be included as a landmark in one set of anatomical landmarks but not included as a landmark in another set of anatomical landmarks) or may comprise a different number of landmarks (for example, 100 rather than 127).

In the present embodiment, for each of the set of 127 anatomical landmarks, the landmark location unit 26 determines whether that landmark is present in the imaging data set 100 by using a classification method to determine whether the relevant anatomy is present. For example, for the anatomical landmark defined at the center of the right eye, the landmark location unit determines whether the center of the right eye is present in the imaging data set 100 by using a trained classifier. If the relevant anatomy is not present, the landmark location unit 26 returns no coordinates for the anatomical landmark in the imaging data set 100.

If the relevant anatomy is present, the landmark location unit 26 determines the location of the landmark in the imaging data set 100 as a set of coordinates in the coordinate space of the imaging data set 100. For example, the landmark location unit 26 determines the position of the center of the right eye as a point in the imaging data set, and returns the coordinates of that position. The determined location of the landmark is specific to the particular imaging data set 100. A similar process of detection and location is performed for each of the set of 127 known anatomical landmarks.

Once the landmark location unit 26 has determined which of the 127 possible landmarks is present in the imaging data set 100, and has determined the location of each of the landmarks that is present, the landmark location unit 26 passes a list of landmark locations, each associated with a respective anatomical landmark, to the registration unit 28.

In the present embodiment, the processing unit 26 detects the anatomical landmarks automatically using classifiers. Detection and localization of pre-defined anatomical landmarks in medical imaging data is performed by a classification forest which uses simple image features. Detection results may be refined with reference to the spatial relationships between the landmarks.

In other embodiments, any other suitable method of landmark detection may be used. Methods of landmark detection may be as described in, for example, Mohammad A Dabbah, Sean Murphy, Hippolyte Pello, Romain Courbon, Erin Beveridge et al, 'Detection and location of 127 anatomical landmarks in diverse CT datasets', *Proc. SPIE* 9034,

*Medical Imaging 2014: Image Processing*, 903415 (Mar. 21, 2014); doi:10.1117/12.2039157; http://dx.doi.org/10.1117/12.2039157; Criminisi, Shotton, Robertson and Konukoglu (2011), 'Regression forests for efficient anatomy detection and localization in CT studies', *Medical Computer Vision. Recognition Techniques and Applications in Medical Imaging*, 106-117; Donner, Menze, Bichof and Langs (2013), 'Global localization of 3D anatomical structures by prefiltered Hough forests and discrete optimization', *Medical Image Analysis*, 17(8), 1304-1314, doi:10.1016/j.media.2013.02.004; or Liu and Zhou, 'Anatomical landmark detection using nearest neighbor matching and submodular optimization', *Medical image computing and computer-assisted intervention (MICCAI)*, 7512, 393-401.

Figure 3:
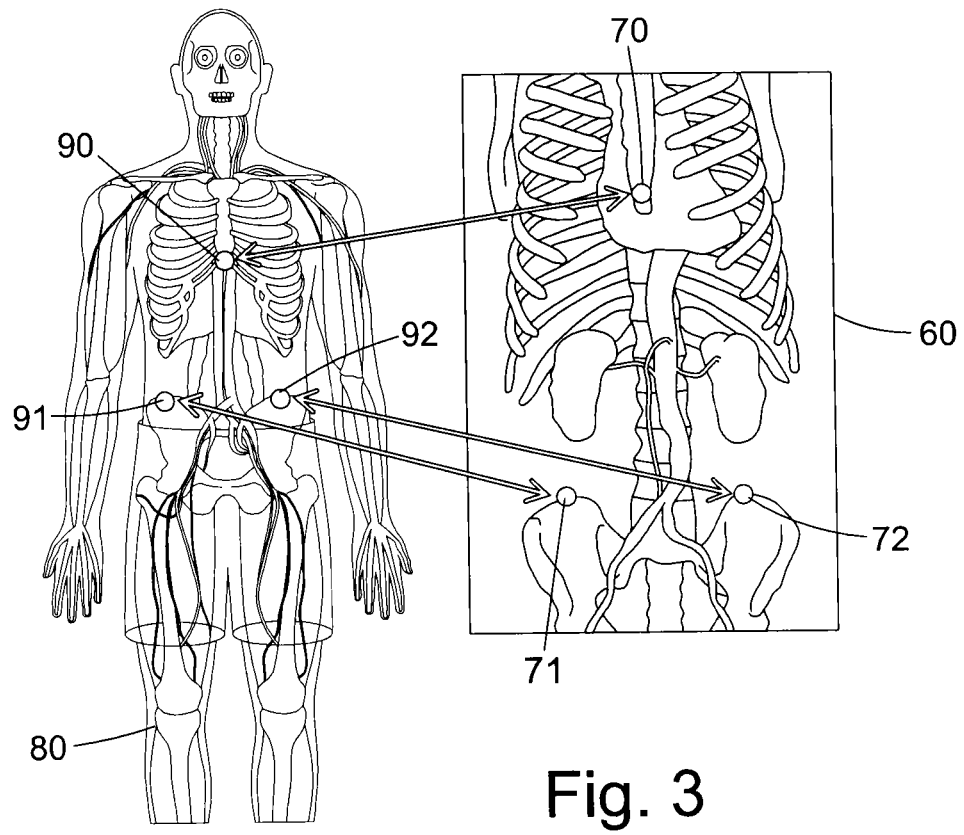
FIG. 3 is an illustration of corresponding landmarks in medical imaging data and virtual anatomy data.

FIG. 3 shows a medical image 60 which has been derived from an imaging data set 100 associated with a patient. The positions of three anatomical landmarks have been marked on the medical image 60: the inferior tip of the sternum 70, the superior aspect of the right iliac spine 71, and the superior aspect of the left iliac spine 72.

At stage 44, the registration unit 28 receives a list of landmark locations 110 pertaining to a mesh-based virtual anatomy data set 120 from memory store 20, or from an alternative data store. In the present embodiment, the mesh-based virtual anatomy data set 120 is Zygote Body (see for example, Kelc R., Zygote Body: A New Interactive 3-Dimensional Didactical Tool for Teaching Anatomy. WebmedCentral ANATOMY 2012; 3(1):WMC002903) and the landmark locations within the mesh-based virtual anatomy data set have been pre-determined by an expert, who has manually identified and determined the position of each of the anatomical landmarks in the Zygote Body data set.

In other embodiments, any other pre-existing or pre-determined model-based virtual anatomy data set may be used.

Virtual anatomy data is available that does not comprise voxels. Virtual anatomy data that does not comprise an array of voxels may be referred to as model-based virtual anatomy data. Model-based virtual anatomy data may be virtual anatomy data that represents anatomical structures by defining surfaces or regions in three-dimensional space. Each anatomical structure in a model-based virtual anatomy may, for example, be represented by any appropriate representation of a region or surface such that the boundaries of the anatomical structure are defined in the virtual anatomy. For example, the representation may be a mesh, a function, a set of functions, or one or more virtual objects.

One type of model-based virtual anatomy data that can be used may be mesh-based virtual anatomy data. In mesh-based virtual anatomy data, polygonal meshes may be used to represent anatomical structures.

The model-based virtual anatomy data set may comprise virtual anatomy data in which the virtual anatomy is represented by three-dimensional surfaces or regions or models of such surfaces or regions. The model-based virtual anatomy data set may comprise mesh-based virtual anatomy data. The mesh-based virtual anatomy data set may comprise a plurality of surface meshes and/or a plurality of space-filling meshes.

In some mesh-based virtual anatomies a set of surfaces are defined, each representing the surface of a respective anatomical structure in three dimensions. Each surface is represented by a polygonal mesh which comprises a set of points, the points linked by edges to form polygonal faces. The surfaces may be nested. For example, surfaces representing the surfaces of organs may be nested inside a surface that represents the surface of the skin.

In some mesh-based virtual anatomies a set of three-dimensional objects are defined, each representing the three-dimensional shape and position of a respective anatomical structure. Each three-dimensional object is represented by a respective three-dimensional mesh. For example, in structural modeling (for example, finite element analysis) a space-filling mesh of polyhedra may be employed. A space-filling mesh of polyhedra may comprise a set of vertices in three dimensions, which are joined by edges to form a plurality of polyhedra. In some applications the polyhedra may typically be tetrahedra or cuboids. The spacings between the points in the set of points that form a space-filling mesh may be considerably greater than the voxel spacing would be in a volumetric virtual anatomy that represents the same anatomy.

The model-based virtual anatomy data set may comprise a surface representation that is not mesh-based. Surfaces of anatomical structures may be defined using any appropriate surface representations. For example, the model-based virtual anatomy data set may comprise a surface representation that is based on control points. The surface representation may be based on splines, for example NURBS. Thus, each three-dimensional surface may be determined using splines, for example NURBS (non-uniform rational basis splines). In some virtual anatomies, a three-dimensional region may be defined for each anatomical structure using any appropriate method. For example, each region may be represented by a virtual solid object.

Returning to the present embodiment, the mesh-based virtual anatomy data set 120 represents an entire human body. Therefore, each of the 127 landmarks that is anatomically defined may be identified and located on the virtual anatomy data set.

In alternative embodiments, fewer landmarks are located in the virtual anatomy data set than are anatomically defined for the generic human body (for example, 127 landmarks are defined anatomically on the human body, of which 90 are located in the virtual anatomy data). In some such embodiments, the virtual anatomy data set 120 does not represent the entire body (for example, for particular applications the virtual anatomy data set 120 represents a part of the body, for example the head) and the set of landmark locations 110 includes only the locations of landmarks that are present in the virtual anatomy data set 120.

In the present embodiment, the locations 110 of the anatomical landmarks on the virtual anatomy data set 120 are pre-determined manually by an expert before the start of the process of FIG. 2. Whilst in the present embodiment, the locations of landmarks in the virtual anatomy data set 120 are determined manually, in alternative embodiments, the locations of landmarks in the virtual anatomy data set 120 are determined automatically or semi-automatically using any appropriate landmark location method.

In the present embodiment, it is not required that the determined location of each anatomical landmark in the mesh-based virtual anatomy data set 120 corresponds to a mesh vertex. The location of each anatomical landmark is only required to be a coordinate point in the coordinate system of the virtual anatomy data set 120, which may or may not correspond to a mesh vertex.

In the present embodiment, the locations of the landmarks on the virtual anatomy data set 120 need only be determined once (in the present embodiment, before the process of FIG. 2 is started) and may then be used in numerous instances of the process of FIG. 2. However, in alternative embodiments, anatomical landmarks are identified and located in the virtual anatomy data set as part of stage 44. In some embodiments, the landmark locations 110 for the virtual anatomy data set are determined before, after, or at the same time as the location of landmarks in the medical imaging data set 100.

Landmarks in the virtual anatomy data set 120 may be referred to as virtual landmarks. Each landmark location is a set of coordinates in the coordinate system of the virtual anatomy data set 120. The list of landmark locations 110 that is passed to the registration unit 28 may be referred to as a database of anatomical landmark locations in the virtual anatomy data set.

FIG. 3 shows, along with the medical image 60 derived from the medical imaging data set 100, a virtual anatomy image 80 derived from a mesh-based virtual anatomy data set 120. In the present embodiment, the virtual anatomy image 80 is derived from Zygote Body. In other embodiments, any suitable mesh-based virtual anatomy data set may be used.

The position of each of three landmarks has been marked on the virtual anatomy image 80: the inferior tip of the sternum 90, the superior aspect of the right iliac spine 91, and the superior aspect of the left iliac spine 92 (the same anatomical landmarks that are marked on the medical image 60). It may be seen that, prior to registration, anatomical landmarks in the virtual anatomy image 80 are in different positions from the positions of corresponding anatomical landmarks in the medical image 60.

In the present embodiment, each of the set of landmark locations for the imaging data set 100 and the set of landmark locations 110 for the virtual anatomy data set 120 comprises all of the 127 defined anatomical landmarks. In other embodiments, the set of landmark locations for the imaging data set 100 comprises more or fewer landmarks than the set of landmark locations 110 for the virtual anatomy data set 120. The number of landmarks in the imaging data set 100 need not match the number of landmarks in the virtual anatomy data set 120.

At stage 46, the registration unit 28 establishes a correspondence between the location of each landmark in the medical imaging data set 100 and the location of its corresponding landmark in the virtual anatomy data set 120. For example, as shown in FIG. 3, each of the medical imaging data set 100 and the virtual anatomy data set 120 includes the landmark at the inferior tip of the sternum (70 and 90 respectively). The registration unit 28 associates the location of the landmark at the inferior tip of the sternum 70 in the medical imaging data set 100 with the location of the landmark at the inferior tip of the sternum 90 in the virtual anatomy data set 120.

It is to be expected that the location of each landmark will be different in the imaging data set coordinate space than in the virtual anatomy data set coordinate space, since each anatomical structure of the patient may differ from that of the virtual anatomy in size, shape and location, and the patient may be positioned differently in space from the virtual anatomy.

At stage 48, the registration unit 28 receives the virtual anatomy data set 120 from the memory store 20. The virtual anatomy data set 120 comprises coordinates of each mesh vertex for each mesh in the virtual anatomy data set 120, and edges connecting the mesh vertices. Although in the present embodiment the registration unit 28 receives the virtual anatomy data set 120 after receiving the set of anatomical landmark locations 110 in the virtual anatomy data set, in other embodiments the virtual anatomy data set 120 and the determined set of anatomical landmark locations 110 in the virtual anatomy data set are received at the same time, or the virtual anatomy data set 120 is received before the set of anatomical landmark locations 110.

At stage 50, the registration unit 28 performs a registration of the medical imaging data set 100 and the virtual anatomy data set 120 using the relationship between corresponding landmark locations that was determined at stage 46. In alternative embodiments, the registration unit 28 obtains a registration of the medical imaging data set 100 and the virtual anatomy data set 120 that has been performed by a different unit or on a different computing apparatus. The registration comprises a transformation between the coordinate space of the virtual anatomy data and the coordinate space of the medical imaging data.

The location of each anatomical landmark that is present in the medical imaging data set 100 has a corresponding location for that anatomical landmark in the virtual anatomy data set 120. The aim of the registration process is to transform the medical imaging data set 100 into the coordinate system of the virtual anatomy data set 120 such that the location of each anatomical landmark in the transformed medical imaging data set coincides, as nearly as possible, with the location of the corresponding anatomical landmark in the virtual anatomy data set 120.

While in the present embodiment the medical imaging data set 100 is transformed into the coordinate system of the virtual anatomy data set 120, in other embodiments the virtual anatomy data set 120 is transformed into the coordinate system of the medical imaging data set 100, or both data sets are transformed into the coordinate system of a further data set, for example a further medical imaging data set.

The registration of the medical imaging data set 100 and the virtual anatomy data set 120 comprises determining a transformation from the coordinate system of the medical imaging data set 100 to the coordinate system of the virtual anatomy data set 120 and optimizing that transformation. The transformation is determined based on the locations of anatomical landmarks in the medical imaging data and the locations of corresponding anatomical landmarks in the virtual anatomy data. In the present embodiment, each landmark location is a set of coordinates, and only the landmark locations are used in the determining of the transformation. The information used to determine the transformation does not comprise, for example, intensity information associated with the anatomical landmarks.

In the present embodiment, the transformation comprises an affine mapping of coordinates with 12 degrees of freedom on the medical image and virtual anatomy coordinate systems. In other embodiments, any other suitable transformation may be used.

In the present embodiment, the transformation is calculated using a robust least squares regression. In other embodiments, any suitable method may be used.

In the present embodiment, the transformation is a rigid transformation comprising rotation, translation and scaling. In other embodiments, the transformation is a non-rigid transformation comprising deformation, which may include local deformation.

The registration unit 28 applies the optimized transformation to the medical imaging data set 100, thereby transforming each voxel of the medical imaging data set 100 into the coordinate system of the virtual anatomy data set 120 using a coordinate transformation comprising rotation, translation and/or scaling. In alternative embodiments in which the determined transformation is a non-rigid transformation, a non-rigid registration can be employed by calculating a warp field interpolated from the landmark coordinates.

In other embodiments, registration unit 28 registers the virtual anatomy data set 120 and medical imaging data set 100 by determining a transformation from the coordinate system of the virtual anatomy data set 120 to the coordinate system of the medical image 100, and transforming the virtual anatomy data set in accordance with the determined transformation by transforming the coordinates of the mesh vertices in the virtual anatomy data set 120.

At stage 52 of the process of FIG. 2, the processing unit 30 receives the virtual anatomy data set 120 and the transformed medical imaging data set (which has been transformed into the coordinate system of the virtual anatomy data set). In other embodiments, the processing unit 30 receives the virtual anatomy data set 120, the original medical imaging data set 100, and details of the registration between the virtual anatomy data set 120 and medical imaging data set 100.

The processing unit 30 renders a combined image comprising a virtual anatomy image 80 derived from the virtual anatomy data set and a medical image 60 derived from the medical imaging data set 100, and displays the combined image on display screen 16.

Figure 4:
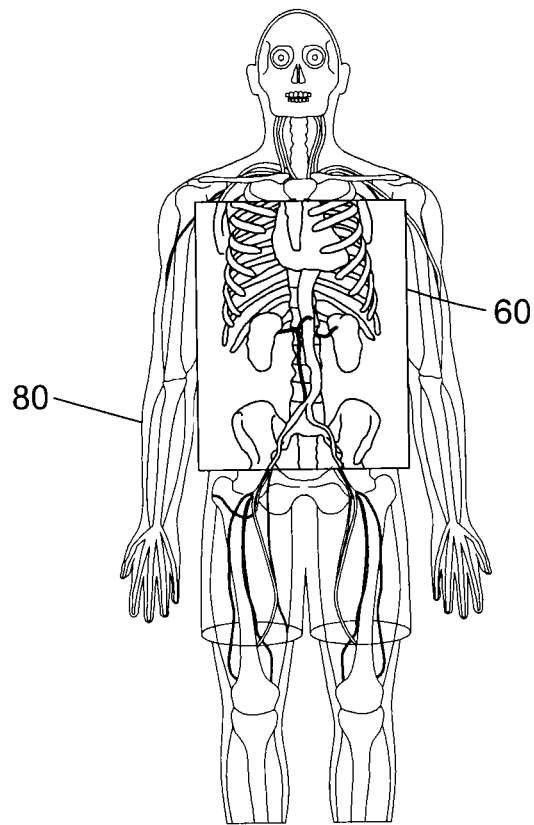
FIG. 4 is an illustration of an overlaid view of virtual anatomy data and medical imaging data.

In the present embodiment, the combined image rendered by the processing unit 30 comprises an overlaid image in which the medical image 60 is overlaid on the virtual anatomy image 80 (the combined image is illustrated in FIG. 4). Since the medical imaging data set has been registered with the virtual anatomy data set, anatomical structures in the medical image 60 are displayed in a location that corresponds to their location in the virtual anatomy image 80. The processing unit 30 displays the overlaid image on display screen 16.

In other embodiments, the processing unit 30 renders an overlaid image in which a virtual anatomy image 80 is overlaid on a medical image 60. In some embodiment, the combined image comprises one part of the body rendered as a virtual anatomy image 80, and another part of the body rendered as a medical image 60. For example, a heart or other organ from the virtual anatomy data set may be shown with lungs or another organ from the medical imaging data set. In some embodiments, the combined image comprises an overlapping image, a merged image, an inset image, a composite image or any other combination of images or imaging data.

In some embodiments, a combined image is rendered by two-dimensional fusion rendering, in which the image value of each voxel in the combined image is a combination of the image value of that voxel in the virtual anatomy image 80 and the image value of that voxel in the medical image 60. In some embodiments a fusion slider is provided by which a user may alter the proportional contributions of the virtual anatomy image 80 and the medical image 60 to the combined image.

In other embodiments, three-dimensional fusion rendering may be used, in which blending of the virtual anatomy with the medical image proceeds volumetrically. Three-dimensional rendering may be accomplished by ray-casting or other methods.

In some embodiments, data derived from the medical imaging data set, such as a multi-planar reconstruction MPR), may be rendered as a combined image with the virtual anatomy data.

One application of a display of a combined image such as that illustrated in FIG. 4 may be to show how the anatomical structures displayed in a medical image 60 relate to the rest of the human body. Although the anatomical structures (for example, the ribs) shown in FIG. 4 may be familiar to most lay people, some medical scans may cover smaller areas or appear more obscure to the lay viewer. In such cases, displaying the medical image 60 overlaid on an image of a representative human body may help the viewer (for example, the patient) to understand the context of their medical scan.

In the present embodiment, the overlaid image comprising the medical image 60 overlaid on the virtual anatomy image 80 may be manipulated by a user. For example, the overlaid image is displayed in a medical image viewing application which allows the user to zoom in or out on the image or to rotate the image. If the user provides an input corresponding to an image manipulation (for example, the user rotates the image using a mouse action), the processing unit 30 renders a new overlaid image which still shows a medical image 60 overlaid on a virtual anatomy image 80, but with each image shown at a new viewing angle corresponding to the user's requested rotation.

In alternative embodiments, at stage 52, instead of rendering a combined image the processing unit 30 renders a medical image 60 in a first frame and a virtual anatomy image 80 in a second frame. The medical image 60 and virtual anatomy image 80 are separate images in separate frames but are aligned with each other using the registration between the medical imaging data set 100 and the virtual anatomy data set 120.

By displaying the medical image 60 and virtual anatomy image 80 in alignment, the images may be displayed such that an anatomical structure that is displayed at a first position in the first frame may be displayed at the same, or a corresponding, position in the second frame. The position of at least one anatomical structure in one of the first frame and the second frame may be dependent on the position of at least one corresponding anatomical structure in the other of the first frame and the second frame. For example, if the top of the head is at the top of the medical image 60 in the first frame, the top of the head may be at the top of the virtual anatomy image 80 in the second frame. Each frame may comprise a window, pane, screen region or display screen or any other display method by which separate images are displayed.

The medical image 60 and virtual anatomy image 80 may be displayed adjacently or in proximity to each other, for example in a horizontal configuration (a side-by-side display) on a single screen, in a vertical configuration, on adjacent screens, or as part of a hanging protocol (in which a plurality of images is displayed, the order and relative positioning of the views being determined by the hanging protocol). Any display may be used that allows both images to be viewed. For example, the images may be displayed overlapping, or it may be possible to toggle between the two images by entering a user input.

In some embodiments, the medical image 60 and virtual anatomy image 80 display at least one anatomical structure that is common to both images. In some embodiments, anatomical structures are displayed such the location and orientation of each anatomical structure is the same, or substantially the same, in the medical image 60 as it is in the virtual anatomy image 80. For example, each of the medical image 60 and the virtual anatomy image 80 may display a view of the patient's head, with the position of the head aligned between the two images (as a result of the registration between the medical imaging data set and virtual anatomy data set).

In some embodiments, the horizontal and/or vertical position of an anatomical structure in the first frame may be the same, or substantially the same, as the horizontal and/or vertical position of a corresponding anatomical structure in the second frame. The corresponding anatomical structure in the second frame may be the same anatomical structure as is shown in the second frame (for example, the skull may be shown in both frames) or may be an adjacent or proximate anatomical structure (for example, the skull may be shown in the first frame and the eyes and other soft tissue in the second frame).

In some embodiments, the position of an anatomical structure in the first frame may be offset from the position of a corresponding anatomical structure in the second frame, for example by a fixed offset value.

The processing unit displays the medical image 60 and virtual anatomy image 80 on display screen 16. One example of a side-by-side display is illustrated in FIG. 5. Another example of a side-by-side display is shown in FIG. 6. Although side-by-side displays are referred to below with regard to the embodiments of FIG. 5 and FIG. 6, similar embodiments exist in which images are arranged vertically, placed on different screens, displayed overlapping, or displayed in any suitable relationship where both images can be viewed.

By showing a medical image 60 adjacent or in proximity to a virtual anatomy image 80, a user may be able to compare the patient's anatomy as shown in the medical image 60 to a representative human anatomy as shown in the virtual anatomy image 80. This may assist a user in identifying anomalies in the patient's anatomy, or in describing such anomalies, for example to the patient.

In some embodiments in which a medical image and a virtual anatomy are shown as separate images (and also in some embodiments in which a combined image is shown), performing an action on one of the medical image 60 and the virtual anatomy image 80 causes a corresponding action to be performed on the other of the medical image 60 and virtual anatomy image 80.

For example, in some embodiments, the processing unit 30 receives a user input from user input device 18 which indicates an action to be performed on the medical image 60. The action to be performed may be any action that may be performed on a medical image, including but not limited to a manipulation such as a rotation, translation or scaling; a change in rendering such as a change of rendering preset, change of color settings, change of intensity or change of transparency; or a selection of a point or region of the image.

The processing unit 30 performs the indicated action on the medical image 60, and also performs a corresponding action on the virtual anatomy image 80. In some embodiment, the corresponding action is an identical action. In other embodiment, the corresponding action is an equivalent action. For example, in one embodiment, the medical image 60 is rendered using a different color scheme from the virtual image 80. When the user requests a change in rendering color or intensity in the medical image 60, a different color or intensity may be applied to the virtual image 80, which is consistent with the relationship between the existing color schemes. For example, in one embodiment in which the medical image is displayed in grayscale and the virtual anatomy image is displayed in color, requesting lighter shades of grey in the grayscale image may result in different colors being used in the virtual anatomy image.

In some embodiments, if the user requests a manipulation (for example, a rotation, translation or zoom) of the medical image 60, the same manipulation is performed on the virtual anatomy image 80. The user may thereby continue to directly compare the images when the images are manipulated.

In some embodiments, selecting a point on the medical image 60 causes the corresponding point to be selected on the virtual anatomy image 80. For example, clicking on a point in the liver or on another organ in the medical image causes a corresponding point on the liver or other organ to be selected in the virtual anatomy image. The selected point is not required to be a landmark or to be part of an identified anatomical structure. Such selection may be used for the placing of measurements, the drawing of regions of interest, or other purposes.

In one embodiment, selecting a point on the medical image 60 (for example, by clicking with a mouse) causes the medical image 60 to be displayed such that the selected point is in the center of the image, and simultaneously causes the virtual anatomy image 80 to be displayed such that the point on the virtual anatomy image that corresponds to the selected point on the medical image is in the center of the virtual anatomy image.

Although the above embodiments are described with reference to an action performed on the medical image leading to a corresponding action in the virtual anatomy image, similar embodiments exist in which an action performed on the virtual anatomy image 80 leads to a corresponding action being performed on the medical image 60.

In some embodiments, semantic information (which may be described as anatomical structure information) associated with the virtual anatomy data set 120 may be used to navigate the registered medical imaging data set. For example, in one embodiment, the location and extent of anatomical structures (for example, bones and organs) in the virtual data set is known, and such structures are labeled. Therefore, it is possible to navigate to particular anatomical structures in the virtual anatomy data set, for example by typing the name of an anatomical structure (e.g. ribs) into a text box.

In one embodiment, typing, for example, 'ribs' or any other name of an anatomical feature into a text box associated with the virtual anatomy image 80 causes the virtual anatomy image 80 to be displayed such that the ribs (or specified anatomical feature) are displayed in the center of the virtual anatomy image 80 (the virtual anatomy image may be described as becoming centered on the ribs). For example, after 'ribs' is typed into the text box, the virtual anatomy image 80 changes to a zoomed-in virtual anatomy image showing the neighborhood of the ribs in the virtual anatomy. In the same embodiment, when the virtual anatomy image 80 becomes centered on the ribs in response to the text input, the medical image 60 also becomes centered on the ribs, the registration of the two data sets being used to provide equivalent views. Therefore the semantic knowledge (anatomical structure labeling) in the virtual anatomy data set may be used to navigate to a given structure in the medical imaging data set, using the registration between the data sets.

In some embodiments, the medical image 60 and the virtual anatomy image 80 are rendered using corresponding rendering presets or other rendering settings. For example, the images may be rendered using the same rendering preset (set of rendering parameters) or equivalent rendering presets.

In some such embodiments, the user may request a change of rendering settings (the user may give a rendering instruction) in one of the images. For example, the user requests a change of rendering settings in the virtual image 80. When the processing unit 30 then renders and displays a new virtual anatomy image 80 with the requested rendering settings, the processing unit 30 also selects rendering parameters for the rendering of the medical image 60 in dependence on the requested rendering parameters for the virtual anatomy image, and renders and displays a new medical image 60 using those rendering settings. Therefore, a rendering instruction applied to one image may be reflected in a corresponding rendering instruction being applied to the other image. In some embodiments, a rendering parameter that is requested for the medical image 60 results in a corresponding rendering parameter being used to render the virtual anatomy image 80. In some embodiments, a rendering parameter that is requested for the virtual anatomy image 80 results in a corresponding rendering parameter being used to render the medical image 60.

The corresponding rendering settings may be the same as the requested rendering settings, or some or all of the rendering settings may differ from the requested rendering settings. For example, in some embodiments, a different rendering method is used to render a virtual anatomy image 80 from the mesh-based virtual anatomy data set 120 than is used to render a medical image 60 from the medical imaging data set 100. Therefore, when a change of rendering settings is requested for the virtual anatomy image 80, a different change in settings, or a change of different settings, may be required to produce the same visual effect in the medical image 80 as is produced in the virtual anatomy image 80.

In the case where a common rendering preset is used for both images, changing the rendering preset for one of the images causes the rendering preset for the other image to be changed, so that the images continue to be displayed using a common preset. Using a common preset may allow the virtual anatomy image 80 and the medical image 60 to be directly comparable.

In other embodiments, different rendering presets or other rendering settings may be applied to the medical image 60 and the virtual anatomy image 80. Using different presets may allow, for example, context to be displayed in the virtual anatomy image 80 that is not displayed in the medical image 60. For example, the medical image 60 may show only bones, while the virtual anatomy image 80 also displays organs.

In some embodiments, a user may select a rendering preset or other rendering parameters for each of the medical image 60 and the virtual anatomy image 80, for example by using a drop-down menu. In some embodiments, the user may choose whether the rendering preset or other rendering parameter is applied to one of the images, or to both of the images.

In the embodiment of FIG. 6, the user may select particular anatomical structures to be highlighted or otherwise emphasized in the virtual anatomy image 80. For example, in FIG. 6, the kidneys 82 are highlighted in the virtual anatomy image 80. In the embodiment of FIG. 6, it may not be possible to isolate a particular anatomical structure (such as the kidneys) for display in the medical image 60. In this case, anatomical structures are not segmented in the medical imaging data set 100 and therefore using a particular preset may return all anatomical structures with similar densities. However, it is possible to render the virtual anatomy image 80 with a highlighted anatomical structure, since the virtual anatomy data set 120 contains the surfaces of each of the anatomical structures, represented as a polygonal mesh. By highlighting anatomical structures in the virtual anatomy image 80, it may be easier to interpret or explain the same structures in the medical image 60.

FIGS. 5 and 6 each show a single medical image 60 and a single virtual anatomy image 80. However, in other embodiments, several medical images 60 and several corresponding virtual anatomy images 80 may be displayed (for example, front, back and side views of each of the medical imaging data and the virtual anatomy data may be displayed simultaneously). In some embodiments, performing a manipulation or a change in rendering parameters on one image (for example, the frontal virtual anatomy image 80) causes the same manipulation or change of rendering parameters to be performed on a corresponding image (for example, the corresponding frontal medical image 60). In other embodiments, each image may be operated on independently.

The embodiments of FIGS. 3, 4, 5 and 6 are each embodiments in which both a medical image 60 and a virtual anatomy image 80 are displayed at stage 52 (for example, as side-by-side images or as an overlaid image comprising the medical image 60 overlaid on the virtual anatomy image 80). However, in other embodiments, only one image (either a medical image 60 or a virtual anatomy image 80) may be displayed.

In one embodiment, a medical imaging data set 100 and virtual anatomy data set 120 are registered using the method of steps 40 to 50 of the process of FIG. 2. The virtual anatomy data set 120 is transformed into the coordinate system of the medical imaging data set 100.

At stage 52, the processing unit 30 renders a medical image 60 from the medical imaging data set 100. Although no image from the registered virtual anatomy data set 120 is displayed, the registered virtual anatomy data set 120 is used to add functionality to the medical imaging data set 100. For example, if a user clicks on a point in the medical image 60 (which may be referred to as a measurement point), the mapping to the virtual anatomy data set 80 can be used to determine a corresponding point in the virtual anatomy data set 80. In the virtual anatomy set, each anatomical structure (for example, each bone and organ) is identified. Therefore, when the user clicks on the measurement point in the medical image 60, the display returns to the user an estimate of which anatomical structure contains the clicked point. The virtual anatomy data set may therefore be used as an atlas (which may in this embodiment be described as a coarse atlas).

Conversely, if the user requests a particular structure or location in the medical image 60, for example by typing 'liver' or the name of another organ into a text box, the definition of that structure or location in the virtual anatomy data set 120 may be mapped onto the medical imaging data set 100 in order to locate or navigate to that structure or location. For example, in one embodiment, when 'liver' is typed into the text box, the processing unit 30 determines the location of the liver in the virtual anatomy data set 120, uses that location and the registration of the virtual anatomy data set 120 and medical imaging data set 100 to determine an estimated location for the liver in the medical imaging data set 100, and places a labeled marker where the liver is estimated to be on the medical image 60. In another embodiment, when 'liver' is typed into the text box, the processing unit 30 renders and displays a medical image 60 which has been zoomed in to the area where the liver is estimated to be.

Registration to the virtual anatomy data set may be used for study navigation. Study navigation may be provided without a virtual anatomy image being displayed. For example, in one embodiment, the user selects a desired organ from a menu. In other embodiment, the user types in a name.

By using registration to the virtual anatomy, navigation of a medical image 60 may be provided even when that medical image 60 is derived from a medical imaging data set 100 in which no structures have been segmented. Although some navigation of the medical imaging data set 100 may be available by way of the landmark locations that have been determined for the medical imaging data set, navigation by such landmarks may only be as detailed as the number of landmark coordinates. Navigation using registration to the virtual anatomy data set may provide more accurate navigation.

The registered virtual anatomy data set may be used to determine anatomical context in the medical imaging data set. The virtual anatomy data set may act as an approximate atlas to identify what anatomy might be present around a given region of interest. For example, if a finding is placed in the imaging data, by transforming the location to the virtual anatomy data, it is possible to look up the nearby anatomical structures to ease and/or automate reporting.

In some embodiments, the user clicking on the medical image 60 causes a virtual anatomy image 80 to be overlaid on the medical image 60. For example, the user clicks on a point in the medical image 60 and the processing unit 30 determines from the mapping to the virtual anatomy image 80 that the point is likely to be in the liver. The processing unit 30 renders and displays an image of the liver from the virtual anatomy, overlaid on the medical image 60.

In some embodiments, after registration of the virtual anatomy data set 120 and medical imaging data set 100, only a virtual anatomy image 80 is displayed initially at stage 52. In some embodiments, the virtual anatomy image 80 is used to navigate in the medical imaging data set 100. For example, by selecting an area of the virtual anatomy image 80, a user may select an equivalent part of the medical imaging data set 100 to be displayed as a medical image 60.

Figure 7:
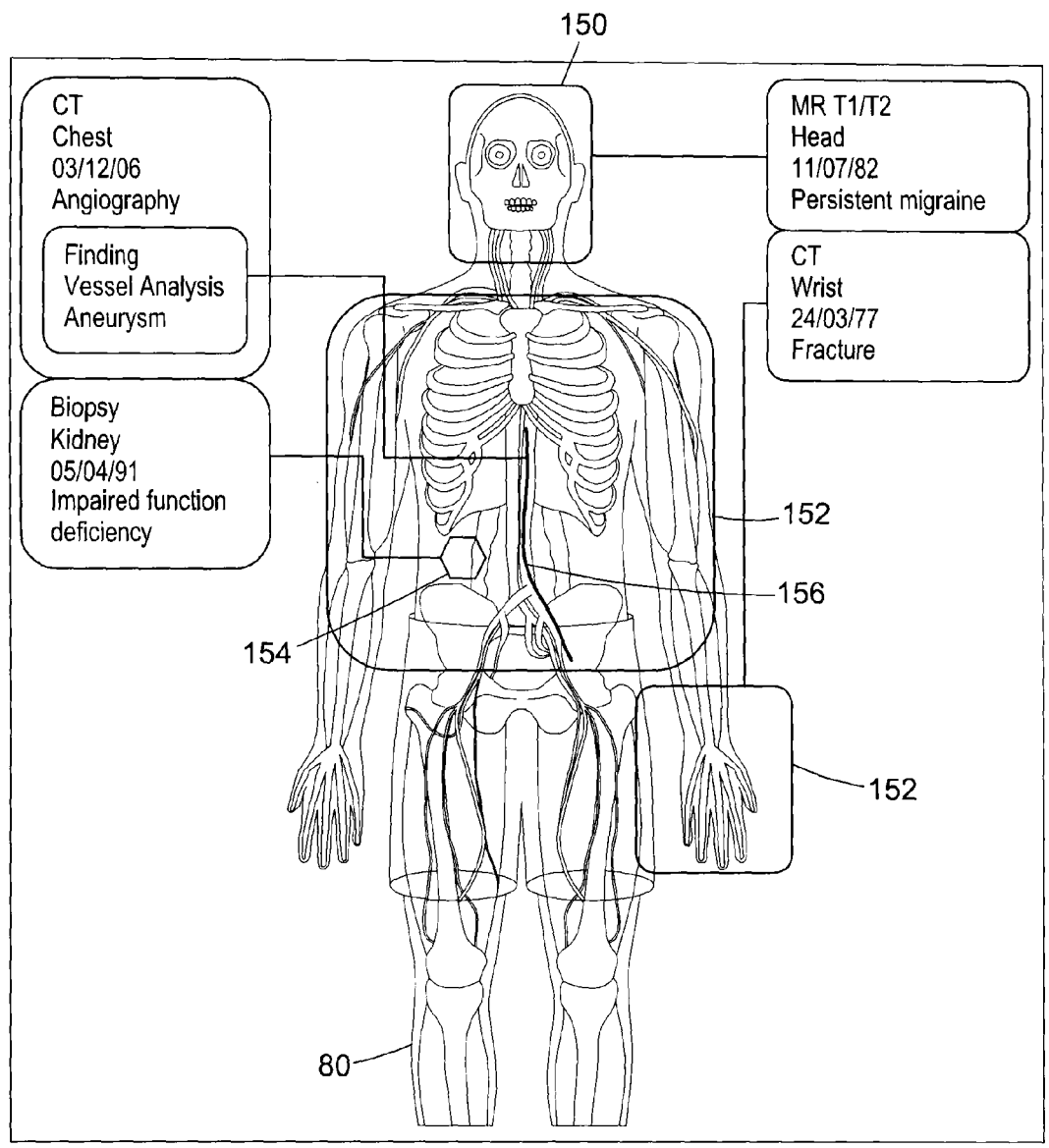
FIG. 7 is an illustration of a virtual anatomy avatar on which patient information is located.

One embodiment using a virtual anatomy image 80 is illustrated in FIG. 7. In the embodiment of FIG. 7, a virtual anatomy image 80 is used as an avatar on which to display patient information. Several indicators 150, 152, 154, 156 are displayed on the virtual anatomy image 80. Each indicator is representative of a scan, finding, or other medical information.

For example, in the embodiment of FIG. 7, an MR scan has been taken of a patient's head. The MR scan is indicated on a virtual anatomy avatar image 80 by an indicator 150. In the present embodiment, the indicator 150 comprises a box which represents the outline of the area covered by the scan. The location and size of the box is determined from a registration of the MR imaging data set with the virtual anatomy data set 120. In other embodiments, the indicator may comprise a region on which a visual effect is applied, for example shading, highlighting, or application of a color. Any representation of a volume, area or boundary of the medical image scan may be used as an indicator.

While in the present embodiment, the indicator 150 comprises an indication of the area of the body that is covered by the scan, in further embodiments the indicator 150 may comprise an indication of the location of the center of the scanned area. In other embodiments, the indicator 150 may comprise an indication of one or more anatomical structures that have been scanned. For example, where the scan is an MR scan of the head, the indicator 150 representative of that scan may be a highlighting or shading of the head, or of a component anatomical structure of the head (for example, the nose, ear, eye or mouth). Where the scan is an MR (or other modality, for example CT or ultrasound) scan of a region comprising the heart, the indicator 150 may be a highlighting or shading of the heart.

In some embodiments, each indicator 150, 152, 154, 156 on the virtual anatomy avatar image 80 may be represented by a different color. In some embodiments, different colors of indicators may correspond to different data types. For example, in one embodiment, indicators 150 representing MR data are shown in green, indicators 152 representing CT data are shown in blue, indicators 154 representing biopsies are shown in orange and indicators 156 representing findings are shown in red. In other embodiments, any color or shading scheme may be used.

In some embodiments, the indicator 150 may be representative of the time at which the medical image scan was taken. For example, the indicator may have a label, text display or color that is representative of the time at which the scan was taken. Different indicators may be colored in dependence on their time relationship (for example, redder for early scans and bluer for later scans).

Also in the embodiment of FIG. 7, the virtual anatomy avatar image 80 displays indicators 152 representing the location and extent of two CT scans (a wrist scan and a chest scan). In the present embodiment, each of the indicators 152 representing a respective CT scan is a box representing the region covered by the scan, and the location and size of each box is determined by registering the respective CT scan imaging data set with the virtual anatomy data set 120.

Other patient information, which does not comprise scan data, may also be indicated on the virtual anatomy avatar image 80 by indicators. For example, in FIG. 7, the virtual anatomy avatar image 80 displays an indicator 154 which indicates the location at which a biopsy has been performed (a kidney biopsy) and an indicator 156 which indicates the location of a finding (an aneurysm). This may be accomplished using a semantic approach (e.g. by an understanding of the anatomical concept of 'kidney' as represented in the virtual anatomy data as a named structure), by a geometric approach (e.g. prior knowledge of the coordinates of the aneurysm associated with the finding) or by other suitable methods.

By registering medical imaging data sets 100 (in this embodiment, two CT data sets and an MR data set) to the virtual anatomy data set 120, indicators 150, 152, 154, 156 may be accurately placed on the virtual anatomy avatar image 80 so that the location and/or extent of a scan, the location of a biopsy, the location of a finding, or the location and/or extent of other medical data may be accurately represented on the virtual anatomy avatar image 80.

The virtual anatomy avatar image 80 may be used as a user interface. In the embodiment of FIG. 7, clicking on an indicator 150, 152, 154, 156 may result in a display of medical data related to that indicator, for example a display of medical data from the scan, biopsy or finding that is represented by that indicator. For example, clicking on an indicator 152 representing the area of the CT scan of the wrist may cause a medical image 60 from the relevant medical imaging data set 100 to be displayed.

Such display of a medical image 60 as a result of clicking on an indicator 152 is not illustrated in FIG. 7, but may comprise display of a medical image 60 along with the virtual anatomy avatar image 80. The displayed medical image 60 may have the same viewing angle and scale as the virtual anatomy avatar 80. For example, a medical image 60 representing a torso scan may be displayed in which the torso has the same size as the torso of the avatar.

In other embodiments, a displayed medical image 60 that is displayed along with the virtual anatomy avatar image 80 may have a different viewing angle or scale from the virtual anatomy avatar image 80. For example, a medical image 60 representing a torso scan may be displayed in which the length of the torso in the medical image 60 is greater than the length of the torso in the virtual anatomy avatar image 80. In some embodiments, the virtual anatomy avatar image is always displayed front-facing, whereas the medical image 60 may be rotated to any appropriate angle.

In other embodiments, clicking on an indicator 152 may cause an appropriate medical image 60 to be displayed in place of the virtual anatomy avatar image 80.

By using the virtual anatomy image 80 as an avatar and user interface, a straightforward and intuitive interface may be presented to a user. The user interface may enable navigation of a complex history. The areas of the patient's body that have been scanned may be accurately represented. Scans taken at different times and of different regions of the body may be represented on a single avatar image. Any data with spatial relevance may be shown on the avatar image.

Figure 8:
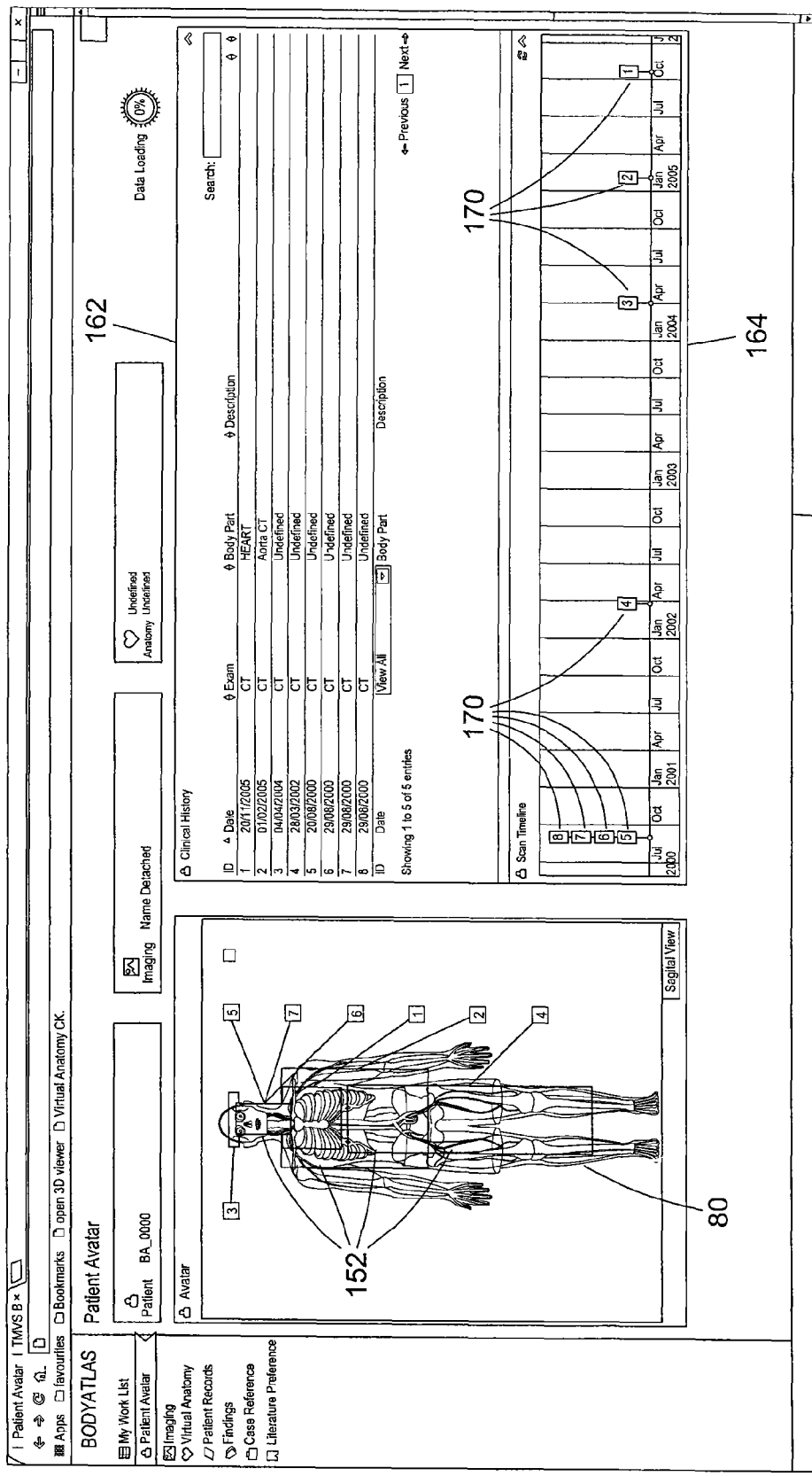
FIG. 8 is an illustration of an exemplary user interface comprising a virtual anatomy avatar, a scan listing and a scan timeline.

In a further embodiment, illustrated in FIG. 8, a virtual anatomy image 80 used as an avatar is part of a wider user interface screen 160. In the embodiment of FIG. 8, the user interface screen 160 comprises a clinical history 162 and a timeline 164. In further embodiments, any other suitable way of representing patient information may be used.

Several medical imaging scans (in this embodiment, CT scans) are represented on the user interface screen 160. Each scan is represented as an indicator 152 and numbered on the virtual anatomy image 80. For each of the medical image scans, the medical imaging data set 100 is registered to the virtual anatomy data set 120. The location and extent of the scan is determined in anatomical terms by the registration to the virtual anatomy data set. The location and extent of the scan are represented on the virtual anatomy image as an indicator 152 comprising a numbered box of the appropriate size and location.

Each medical image scan is also listed in a clinical history 162, in which scan type, anatomical location of scan and scan description are listed for each scan in chronological order. In other embodiments, a different ordering may be used.

Each medical image scan is further represented in a timeline 164 in which time is represented on a time axis. Each scan is represented by an indicator 170 on the timeline (which has the same number with which its indicator is labeled on the virtual anatomy image 80). The indicator 170 on the timeline 164 is placed at a point on the time axis that represents the time at which the image was taken. The placement of the number provides time data related to the scan. Although in the present embodiment, time is represented on a timeline 164, in other embodiments any suitable graphical representation of time may be used, for example a calendar. For each indicator 152 on the virtual anatomy avatar image 80, a corresponding indicator 170 is placed on the graphical time representation.

The clinical history 162 and timeline 164 may additionally display medical events other than image scans, such as a biopsy, surgery, other procedure, or encounter.

By selecting a date by clicking on the appropriate point on the timeline 164, the user may change the display on the virtual anatomy avatar image 80 to show only scans taken before the selected date. In other embodiments, by highlighting or otherwise selecting a time period with the timeline 164, the user may display on the virtual anatomy avatar image 80 only indicators representing scans taken in the highlighted time period. The user may therefore filter scans by time period.

In some embodiments, the processing unit is configured to receive a user selection representative of a point in time (for example, a particular date) or a time period. For example, the user may select a region of the timeline 164, or may type in a time range or select a time range on a calendar. The processing unit is configured to select any of the plurality of indicators on the virtual anatomy avatar image 80 that correspond to the selected time point or date. For example, if the user selects 2008, the processing unit selects any indicators on the virtual anatomy avatar image 80 that correspond to scans taken in 2008.

In some embodiments, selecting one or more of the indicators on the timeline 164 causes the corresponding indicator 152 on the virtual anatomy avatar image 80 to be selected, displayed on the virtual anatomy avatar image 80, or highlighted or otherwise emphasized on the virtual anatomy avatar image 80.

In some embodiments, selecting one or more of the indicators 152 on the virtual anatomy avatar image 80 causes the corresponding indicator on the timeline 164 to be selected on the timeline 164, displayed on the timeline 164, or highlighted or otherwise emphasized on the timeline 164.

In further embodiments, any method of representing scan times may be used. Scans may be represented on the timeline 164 as indicators other than numbers, for example by colors or by text information.

In further embodiments, a virtual anatomy data set 120 is used for surgical planning of surgery on a patient. A surgical plan is defined on the virtual anatomy. The virtual anatomy data set 120 is then registered to a medical imaging data set 100 comprising the area of the patient on which surgery will be performed. The virtual anatomy data set 120 is transformed into the coordinate system of the medical imaging data set 100, defining the surgical plan on the patient's anatomy.

Virtual anatomy data may be linked to standard ontologies. By associating the identity of organs and structure in the virtual data with objects in a standard anatomical ontology (for example, the Foundational Model of Anatomy), improved interoperability with other healthcare systems may be possible. For example, the ontology may be used to semantically analyze the text of medical records or reports in order to identify anatomical terms; these terms may then by automatically linked to the relevant anatomical structures in the virtual anatomy data. This link may be represented by a hypertext mark-up of the relevant text, enabling the user to display the relevant virtual anatomy.

By mapping a generic, structural description of human anatomy to the medical imaging data of a given patient, value may be added to imaging applications in a range of areas, including teaching, anatomical reference, navigation, communication of results to a referring clinician and/or to a patient, and ease of interpretation. By displaying a virtual anatomy image and a medical image of the same anatomy (as determined by the registration) it may become easier to explain or interpret the medical image. A user, for example a student, may be able to use the registration of the medical imaging data to the virtual anatomy data to navigate in the medical image, even when the medical image has not been segmented. The use of the virtual anatomy for navigation may not require a virtual anatomy image to be displayed. By displaying a medical image overlaid on, or side-by-side with, a virtual anatomy, a clinician may be able to provide context when explaining scan results to a patient.

Each of the embodiments described above uses anatomical landmarks to establish mapping between patient data and a mesh-based virtual anatomy. Other approaches use image-based registration of patient data and a volumetric virtual anatomy. However, image-based registration is more computationally intensive, hence slower, than mapping between landmarks.

Using landmarks may provide a relatively quick, computationally efficient method of registering patient data and mesh-based virtual anatomy data. Only a relatively small number of points in each data set (for example 127 or fewer points in above embodiments) is required to be identified and located. The registration of images using landmarks may be performed using known methods. Anatomical landmarks may be clearly defined anatomically, such that the matching of corresponding points in different data sets may be likely to be accurate.

Furthermore, it may not be possible to map volumetric patient data to mesh-based virtual anatomy data using image similarity based registration techniques, because the required voxels and voxel intensities may not be defined in mesh-based virtual anatomy data. Using landmarks may allow for mesh-based virtual anatomy data to be registered with patient data where such a registration may not be possible using some other techniques.

Many virtual anatomy data sets currently available are mesh-based. Mesh-based data may be easier to render than volumetric data and may be visualized more flexibly. Mesh-based data may be better than volumetric data in capturing a non-patient-specific representation of a generic human anatomy. The approach of the above embodiments can therefore work with data that may be easier to obtain, easier to render, more flexible and more suitable than volumetric virtual anatomy data.

Other approaches to mapping virtual anatomy data to real patient data may comprise using semantic information. Semantic information (for example, the name of an organ) only gives an approximate position, whereas landmarks may give accurate positions for particular points in the body. Except in specific cases (for example, involving secondary captures), the organ or structure relevant to an item of semantic data may not be able to be easily determined. The use of the above embodiments may be more accurate and more flexible than mapping using semantic data.

It is known to align images using fiducials (physical markers) for marking locations in or on a patient. However, the use of fiducials is not common outside specialized procedures. The method of the above embodiments does not require physical markers.

Certain embodiments provide a method for registering medical imaging data with virtual anatomy data comprising a means for automatically determining anatomical landmark locations in volumetric medical imaging data, a database of corresponding anatomical landmark locations in mesh-based virtual anatomy data, and a means of establishing a transformation between the medical imaging coordinate space and the virtual anatomy coordinate space.

In some embodiments, the registration of the medical imaging data with the virtual anatomy data comprises a rigid registration. In some embodiments, the registration of the medical imaging data with the virtual anatomy data comprises a non-rigid registration.

In some embodiments, an apparatus is provided in which side-by-side registered display of medical imaging data and virtual anatomy data is enabled. In some embodiments, an apparatus is provided in which fusion display of medical imaging data and virtual anatomy data is enabled. In some embodiments, the correspondence between the virtual anatomy data and the medical imaging data is exploited to provide information on the anatomical context of a location in the medical imaging data.

In some embodiments, an apparatus is provided that accurately shows the location of a medical imaging data set, a region of interest or a finding on a virtual anatomy user interface display.

Although particular embodiments have been described above, features of any embodiment may be combined with features of any other embodiment.

Although the detection and location of landmarks has been described in relation to landmarks that each comprise a single point in an imaging data set, for example a single pixel or voxel, it will be understood that in alternative embodiments each landmark may comprise any suitable imaging data item, for example a larger block of imaging data representing a region larger than a single pixel or voxel.

It will be well understood by persons of ordinary skill of the art that embodiments may implement certain functionality by means of a computer program or computer programs having computer-readable instructions that are executable to perform the method of the embodiments. The computer program functionality could be implemented in hardware. The embodiments may be implemented by one or more ASICs (application specific integrated circuit) or FPGAs (field programmable gate arrays) or by a mix of hardware or software.

Whilst particular units have been described herein, in alternative embodiments functionality of one or more of these units can be provided by a single processing resource or other component, or functionality provided by a single unit can be provided by two or more components in combination. Reference to a single unit encompasses multiple components providing the functionality of that unit, whether or not such components are remote from one another, and reference to multiple units encompasses a single component providing the functionality of those units.

Whilst certain embodiments have been described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An image processing apparatus, comprising
a data receiving unit configured to receive medical imaging data;
a registration unit configured to obtain a registration of the medical imaging data and model-based virtual anatomy data by determining a transformation between a coordinate space of the medical imaging data and a coordinate space of the virtual anatomy data based on the locations of anatomical landmarks in the medical imaging data and the locations of corresponding anatomical landmarks in the virtual anatomy data, wherein the model-based virtual anatomy data comprises a synthetic, non-patient specific representation of generic human anatomy in three dimensions;
a virtual image generator configured to render images derived at least in part from the virtual anatomy data, the medical imaging data, and the registration obtained by the registration unit;

a display configured to display the rendered images wherein at least one of the rendered images is derived from the medical imaging data and at least one of the rendered images is derived from the virtual anatomy data; and a processing unit configured to display in a first frame a medical image derived from the medical imaging data and to display in a second frame a virtual anatomy image derived from the virtual anatomy data, wherein the medical image in the first frame and the virtual anatomy image in the second frame are aligned in accordance with the registration of the medical imaging data with the virtual anatomy data.

2. An apparatus according to claim 1, wherein the model-based virtual anatomy data comprises mesh-based virtual anatomy data.

3. An apparatus according to claim 1, wherein the model-based virtual anatomy comprises at least one of a) and b):
a) a plurality of representations of three-dimensional surfaces, each representative of a respective anatomical structure;
b) a plurality of representations of three-dimensional regions, each representative of a respective anatomical structure.

4. An apparatus according to claim 3, wherein the virtual anatomy data comprises three-dimensional surfaces determined by control points.

5. An apparatus according to claim 1, wherein the medical image in the first frame and the virtual anatomy image in the second frame are aligned such that the position of at least one anatomical structure in one of the first frame and the second frame is dependent on the position of at least one corresponding anatomical structure in the other of the first frame and the second frame.

6. An apparatus according to claim 1, wherein at least one of:
the horizontal position of the first frame or each anatomical structure in the first frame is substantially the same as the horizontal position of the second frame or each corresponding anatomical structure in the second frame;
the vertical position of the first frame or each anatomical structure in the first frame is substantially the same as the horizontal position of the second frame or each corresponding anatomical structure in the second frame;
the position of the first frame or each anatomical structure in the first frame is offset from position of the second frame or each corresponding anatomical structure in the second frame by an offset value.

7. An apparatus according to claim 1, wherein the processing unit is configured to select at least one rendering parameter to render one of the medical image and the virtual anatomy image in dependence on at least one rendering parameter used to render the other of the medical image and the virtual anatomy image.

8. An apparatus according to claim 1, wherein the processing unit is further configured to receive at least one user input representative of an action to be performed on one of the medical image and the virtual anatomy image, to perform the action on the one of the medical image and the virtual anatomy image, and to perform a corresponding action on the other of the medical image and the virtual anatomy image.

9. An apparatus according to claim 8, wherein the action comprises at least one of: a rotation, a translation, a scaling, and a rendering.

10. An apparatus according to claim 8, wherein the action comprises a user selection of a point or region, and the corresponding action comprises the selection of a corresponding point or region.

11. An apparatus according to claim 1, wherein the combined image comprises rendered images include at least one of: an overlaid image, a merged image, a fusion rendered image, an overlapping image, an inset image, and a composite image.

12. An apparatus according to claim 1, wherein the virtual anatomy data comprises or is associated with anatomical structure information, and wherein the processing unit is configured to receive a user selection of a point or region of the medical image and to identify an anatomical structure corresponding to the selected point or region of the medical image based on the anatomical structure information and the registration of the medical imaging data and the virtual anatomy data.

13. An apparatus according to claim 1, wherein the virtual anatomy data comprises or is associated with anatomical structure information, wherein the processing unit is configured to receive a user input indicative of an anatomical structure and to indicate the anatomical structure on the medical image based on the anatomical structure information and the registration of the medical imaging data with the virtual anatomy data.

14. An apparatus according to claim 1, further comprising said processing unit is configured to display said virtual anatomy image from virtual anatomy data comprising an indicator indicating a location associated with a medical image scan.

15. An apparatus according to claim 14, wherein the indicator comprises at least one of a), b), c) and d):
a) a representation of a volume, area or boundary of the medical image scan;
b) an indicator representative of the location of the center of the medical image scan;
c) an indicator representative of an anatomical region or structure in the medical image scan;
d) an indicator representative of the time at which the medical image scan was taken.

16. An apparatus according to claim 14, wherein the processing unit is further configured to receive a user selection of the indicator, and in response to the user selection to display a medical image derived from medical imaging data from the medical image scan associated with the selected indicator.

17. An apparatus according to claim 14, wherein the processing unit is configured to display a virtual anatomy image from the virtual anatomy data comprising a plurality of indicators each indicating a location associated with a respective medical image scan, and wherein the processing unit is configured to display a graphical time representation, wherein each indicator on the virtual anatomy is associated with a corresponding indicator on the graphical time representation.

18. An apparatus according to claim 17, wherein the processing unit is configured to receive a user selection representative of a point in time or time period, and to select at least one of the plurality of indicators on the virtual anatomy image that corresponds to the selected point in time or time period.

19. An apparatus according to claim 17, wherein the processing unit is configured to receive a user selection of at least one of the plurality of indicators on the virtual anatomy image, and to select each corresponding indicator on the graphical time representation.

20. An apparatus according to claim 1, further comprising a landmark location unit configured to locate each landmark in the medical imaging data.

21. An apparatus according to claim 1, wherein registration of the medical imaging data to the virtual anatomy data comprises at least one of a rigid registration and a non-rigid registration.

22. An apparatus according to claim 1, wherein the medical imaging data comprises volumetric medical imaging data.

23. An apparatus according to claim 22, wherein the volumetric medical imaging data comprises at least one of CT data, MRI data, Cone Beam CT data, PET data, SPECT data or ultrasound data.

24. An image processing method comprising;
receiving medical imaging data;
obtaining a registration of the medical imaging data and model-based virtual anatomy data, comprising determining a transformation between a coordinate space of the medical imaging data and a coordinate space of the virtual anatomy data based on the locations of anatomical landmarks in the medical imaging data and the locations of corresponding anatomical landmarks in the virtual anatomy data, wherein the model-based virtual anatomy data comprises a synthetic, non-patient specific representation of generic human anatomy in three dimensions;
rendering images derived at least in part from the virtual anatomy data, the medical imaging data, and the registration obtained in the obtaining step; and
displaying the rendered images wherein at least one of the rendered images is derived from the medical imaging data and at least one of the rendered images is derived from the virtual anatomy data; and
displaying in a first frame a medical image derived from the medical imaging data and displaying in a second frame a virtual anatomy image derived from the virtual anatomy data,
wherein the medical image in the first frame and the virtual anatomy image in the second frame are aligned in accordance with the registration of the medical imaging data with the virtual anatomy data.

25. A non-transitory computer-readable storage medium storing a computer program for performing a method according to claim 24.

* * * * *